United States Patent [19]
Karafa et al.

[11] Patent Number: 5,012,117
[45] Date of Patent: Apr. 30, 1991

[54] PROCESS AND APPARATUS FOR THE AUTOMATIC NON-CONTACT SURFACE INSPECTION OF CYLINDRICAL PARTS

[75] Inventors: Nandor Karafa, Wuppertal; Lutz Liebers, Essen, both of Fed. Rep. of Germany

[73] Assignee: Alfred Teves GmbH, Frankfurt Am Main, Fed. Rep. of Germany

[21] Appl. No.: 404,239

[22] Filed: Sep. 7, 1989

[30] Foreign Application Priority Data

Sep. 15, 1988 [DE] Fed. Rep. of Germany ....... 3831401

[51] Int. Cl.$^5$ .............................................. G01N 21/88
[52] U.S. Cl. .................................... 250/572; 356/446
[58] Field of Search ............... 250/223 B, 223 R, 571, 250/572 O; 356/237, 429, 430, 446, 426, 428, 241

[56] References Cited

U.S. PATENT DOCUMENTS

| | | | |
|---|---|---|---|
| 3,812,349 | 5/1974 | Gugliotta et al. | 250/223 R |
| 3,829,220 | 8/1974 | Parkinson | 250/571 |
| 3,870,890 | 3/1975 | Binks et al. | 250/571 |
| 3,907,438 | 9/1975 | Holeman | 356/156 |
| 3,918,816 | 11/1975 | Foster et al. | 356/167 |
| 4,007,992 | 2/1977 | Petrohilos et al. | 250/571 |
| 4,043,673 | 8/1977 | Harris et al. | 250/571 |
| 4,203,673 | 5/1981 | Buckson | 356/446 |
| 4,276,910 | 7/1981 | Eichenberger | 250/571 |
| 4,358,202 | 11/1982 | Puffer | 356/237 |
| 4,831,250 | 5/1989 | Fukuchi et al. | 250/223 B |
| 4,866,263 | 9/1989 | Fukuchi | 250/223 B |

Primary Examiner—David C. Nelms
Assistant Examiner—Stephone B. Alen
Attorney, Agent, or Firm—Robert P. Seitter; J. Gordon Lewis

[57] ABSTRACT

A process and an apparatus for its realization are provided for an automatic non-contact surface inspection of cylindrical parts. The parts under inspection are imparted a rotary motion about their axis of symmetry and are exposed to largely parallel light whose diffused portion reflected by the surface of the parts is evaluated optoelectronically.

21 Claims, 1 Drawing Sheet

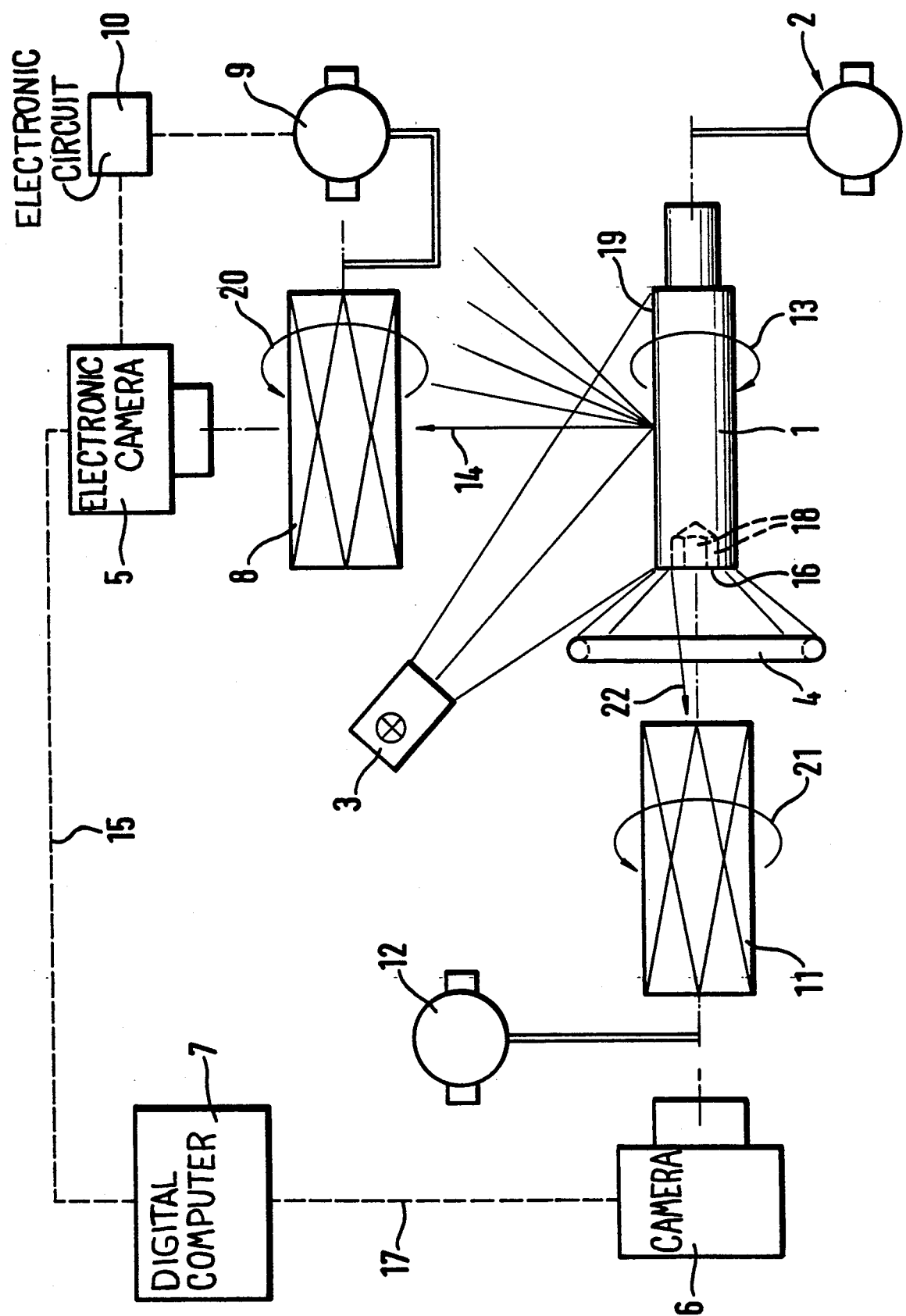

PROCESS AND APPARATUS FOR THE AUTOMATIC NON-CONTACT SURFACE INSPECTION OF CYLINDRICAL PARTS

BACKGROUND OF THE INVENTION

The present invention relates to a process for the automatic non-contact surface inspection of cylindrical parts and to an apparatus for its realization.

In order to meet the rigid requirements established today in the industry for parts to be mounted, a series of quality assuring measures are needed, including, among others, an inspection of the surface properties of the parts. This inspection is presently carried out visually, that is, for example, the parts are constantly observed by two persons in the course of manufacture on two visual inspection lines arranged parallel to each other. In this manner, the inspectors may manually sort out parts presenting surface defects. During this procedure, both the surface and the contact surface are inspected for any surface damages and for the penetration of foreign particles in the grip of the tool which may handle the parts. In this way, the inspected parts can be mounted with assurance by the ultimate user by automatic assembly methods.

It is disadvantageous in inspections of this kind that reliability exclusively depends on persons, so that a "zero-error requirement" cannot be met due to the heavy psychological stress on the inspection personnel which is due at least in part, to the large number of workpieces to be inspected during this procedure.

It is, therefore, an object of the present invention to provide a process which renders it possible to avoid the disadvantages of the prior art in that an automatic non-contact surface inspection of the cylindrical parts is carried out by a fully automatic, mechanized image processing station.

It shall be possible simultaneously to detect the following kinds of defects:
 (a) grooves and scores;
 (b) excessively rough surface in general;
 (c) radially directed indentations;
 (d) striking and blow marks;
 (e) incompleteness of surfaces regarding the shaping of edges;
 (f) existance/non-existance of foreign matter at inside surfaces of application of force at a front side of a workpiece; and,
 (g) differentiation between inevitable or admissible lubricant residues and real defects at the barrel surface.

Another object of the invention is to provide a suitable apparatus for realizing the process.

SUMMARY OF THE INVENTION

In order largely to eliminate the portion of light which is directionally reflected during illumination of the parts to be inspected and which causes a disturbance variable in the event of the photoelectronic scanning, it is provided in accordance with the present invention that the barrel surface of the parts under inspection is exposed to the light rays at an oblique angle of preferably about 35 degrees. In order to inspect the inside surfaces of application of force at the front side of the parts to be inspected for the absence of accidentally intercalated foreign matter, it is provided according to the present invention that the front surface of the parts to be inspected is exposed to an axially symmetrical illumination.

According to another advantageous embodiment of the inventive process, the diffused portion of light is scanned by means of an electronic camera, the parts under inspection being rotated 360 degrees during the scanning.

According to a particularly advantageous embodiment of the inventive apparatus, a first source of light is provided to illuminate the barrel surface of the parts to be inspected and a first camera for the relevant scanning and a second source of light to illuminate the front surface of the parts to be inspected and a second camera for the relevant scanning.

According to a further embodiment of the apparatus in accordance with the present invention, the first source of light is formed by a halogen lamp with succeeding reflector concentrating the light rays. By this provision, a sufficient luminous intensity easily allowing to be controlled varying the lamp voltage is achieved. Further advantages are a favorably directed light, a longer service life and low costs of replacement lamps.

In another embodiment of the apparatus, the first source of light is formed by a stroboscopic flashtube. An absolutely clear image is achieved by this measure, since no lack of sharpness due to motion is caused due to very short flashes (typically below 10 exp −5 sec.).

According to another advantageous feature of the invention, the first source of light may be formed by superbright light emitting diodes in order to achieve a small overall size of the first source of light. This provision renders predetermined geometric arrangements (such as a ring) and a pulses emission of light.

According to a further advantageous embodiment of the inventive apparatus, the second source of light is formed by an axially symmetrical arrangement of a plurality of electric bulbs. The light emitted illuminates a foreign body in a cavity from all sides, but it cannot directly penetrate into the interior space of the cavity, so that the latter appears black to the camera.

The camera which scans the surface of the parts to be inspected is preferably configured as a matrix camera. In order to avoid the unsharpness due to motion caused by extended exposure times which are inherent to the principle of the matrix camera, according to the invention a synchronously rotation rotary prism is disposed between the electronic camera and the parts under inspection which creates a parallel shift of the path of the rays. It is an advantage offered by this measure that the trace of the rays emitted by the rotating surface of the cylindrical part is panned within a certain range. In this configuration, the rotary prism preferably presenting at least four planes is drivable by a synchronous motor or stepping motor, an electronic circuit being provided with the aid of which a fixed phase relation is adjustable between the picture shooting cycles of the camera and the angle of rotation of the rotary prism.

According to another advantageous embodiment of the inventive apparatus between the front surface of the part to be inspected and the camera which scans the front surface, a second rotary prism is arranged which furnishes the camera with a straight-lined path of rays. This arrangement has a significant characteristic: rotation the prism through an angle alpha, the scenery behind the prism will apparently rotate through two time alpha. This effect is utilized in the following manner: the camera scanning the front surface views the rotating front surface through this prism. The prism is accommodated in a housing furnished with a pivot bearing and is driven by a small gearmotor at half the number of revolutions of the rotation test piece. The senses of rotation of the cylindrical parts and of the prism are inverse relative to each other. The camera, thus, views a cylindrical part at rest around which the slewing mechanism rotates.

BRIEF DESCRIPTION OF THE DRAWING

In the following, the inventive process and the apparatus for its realization will be described in more detail with reference to the accompanying drawing the single FIGURE of which illustrates diagrammatically one embodiment of the apparatus according to the present invention.

DETAILED DESCRIPTION

The drawing shows one embodiment of the apparatus in accordance with the principles of the present invention for the automatic non-contact surface inspection of cylindrical parts with a slewing mechanism 2 driven by an electric motor with the aid of which the cylindrical parts, such as for example pin 1, being fed one after the other by means of a conveying mechanism (not shown) are imparted a rotary motion in the sense outlined by the arrow 13. Two sources of light 3, 4 are provided for the illumination of the rotating pin 1. The first source of light 3 which may be formed by a halogen lamp, by a stroboscopic flashtube or by superbright light emitting diodes is preferably arranged in such a manner that it renders illumination of the barrel surface of the pin at an oblique angle, for example, at an angle of approximately 35 degrees. The reflected diffused portion (being symbolically illustrated by an arrow 14 in the drawing) of the virtually parallel light emitted by the first source of light 3 enters a first electronic camera 5, preferably a matrix camera, whose output signals are fed to a digital computer 7 through a signal line 15 shown by a dashed line in the drawing, a first rotary prism 8 being interposed between the first source of light 3 and the first camera 5. Rotary prism 8 presents at least four planes and is driven by a synchronous or stepping motor 9 which is activated by means of an electronic circuit 10 in such a manner that a fixed phase relation between the picture shooting frequency of the first camera 5 and the angle of rotation of the first rotary prism 8 is achieved.

The front surface 16 of the pin 1 to be inspected which presents a plurality of surfaces of application of force 18 and is illuminated by the second source of light 4 being, for example, arranged in the shape of an illumination ring is scanned by means of a second matrix camera 6 whose output signals are fed to digital computer 7 through a second signal line 17, a second rotary prism 11 being interposed between second source of light 4 and second camera 6. Second rotary prism 11 preferably is arranged as a direct-vision prism is driven by a gearmotor 12. The two rotary prisms 8, 11 are preferably arranged in such a manner that whereas the axis of rotation of first rotary prism 8 forms an angle of 90 degrees with the optical axis of said first matrix camera 5, the axis of rotation of said second rotary prism 11 runs parallel with the optical axis of second matrix camera 6.

The method of functioning of the inventive apparatus is described as follows: In the event of illumination of the barrel surface 19 of the rotation pin 1, the incident light will be reflected in two different ways. The major portion of it will be reflected directionally, which means that it will leave the barrel surface 19 at the identical angle at which it struck it. The definitely smaller portion will be reflected diffusedly, that is to say, it will be scattered to all sides. Since the directionally reflected rays do not contain any evaluable share of image information, they will skirt the first matrix camera 5. The diffusedly reflected rays contain the evaluable image information and through the first rotary prism 8 enter the lens of the first matrix camera 5, the sense of rotation of said first rotary prism 8 (arrow 20) being contrary to the sense of rotation of the rotating pin 1. First rotary prism 8 causes a parallel shift of the path of the rays by the measure by which the barrel surface 19 of the pin 1 also will have moved on in the scanned range. By this measure, the necessary definition of the image is obtained. The electronic circuit 10 mentioned above will ensure that the path of the rays of the diffused portion of light enters the first matrix camera 5 at the right moment. The image information recorded by the first matrix camera 5 is subsequently evaluated in the digital computer 7 on the basis of different programs which have specifically been prepared to detect a determined kind of defect.

By the scanning of the front surface 16 of the pin 1 it is checked whether or not there are foreign particles in the surfaces of application of force 18. In this context, the second source of light 4 is preferably arranged such that the bottom of the surfaces of application of force 18 (e.g., of a hexagonal recess) remains free of directly striking light. The path of rays 22 being reflected by the front surface 16 enters the second matrix camera 6, penetrating on its way through the second rotary prism 11 which rotates contrary to the rotation pin 1 (arrow 21) and by the use of which a considerable improvement of the image quality results. As a further result, evaluability by computer is attained because the unsharp definition of the image due to the motion of the rotation pin 1 is balanced. The image information of the second matrix camera 6 is again evaluated in the digital computer 7 by a suitable program.

What is claimed is:

1. An apparatus for the automatic non-contact surface inspection of cylindrical parts comprising, in combination:
    a slewing mechanism (2) driven by an electric motor and accommodating said parts (1) to be inspected;
    at least one source of light (3, 4) to illuminate said part (1) to be inspected;
    at least one electronic camera (5, 6) scanning the surface of said parts (1) to be inspected one after the other at a time interval; and,
    a digital computer (7) succeeding said electronic camera (5, 6) and serving to evaluate the image information transmitted by the latter wherein a first source of light (3) illuminates the barrel surface (19) of said parts to be inspected and a first one of said camera (5) for the relevant scanning and a second said source of light (4) to illuminate the front surface (16) of said part to be inspected and a second one of said camera (6) for the relevant scanning.

2. An apparatus as claimed in claim 1, wherein said first source of light (3) is formed by a halogen lamp with succeeding reflector concentrating the light rays.

3. An apparatus as claimed in claim 1, wherein said first source of light (3) is formed by a stroboscopic flashtube.

4. An apparatus as claimed in claim 1, wherein said first source of light (3) is formed by superbright light emitting diodes.

5. An apparatus as claimed in claim 1 wherein said second source of light (4) is formed by an axially symmetrical arrangement of a plurality of electric bulbs.

6. An apparatus as claimed in claim 1, wherein a first rotary prism (8) which rotates synchronously with the picture shooting frequency of said firs camera (5) and which creates a parallel shift of the reflected path of the rays is disposed between said first electronic camera (5) and said parts (1) under inspection.

7. An apparatus as claimed in claim 6, wherein said first rotary prism (8) is drivable by a synchronous motor or stepping motor (9), an electronic circuit (10) being provided by which a fixed phase relation is adjustable between the picture shooting cycles of said first camera (5) and the angle of rotation of said first rotary prism (8).

8. An apparatus as claimed in claim 7, wherein first rotary prism (8) presents at least four planes.

9. An apparatus a claimed in claim 1, wherein between the front surface (16) of said part (1) to be inspected and said second camera (6) a second rotary prism (11) is arranged which furnishes said second camera (6) with a straight-lined path of rays.

10. An apparatus as claimed in claim 9, wherein said second rotary prism (11) is drivable by a gearmotor (12).

11. An apparatus as claimed in claim 10, wherein the rate of revolutions of the said second rotary prism (11) corresponds to half the rate of revolutions of said part (1) to be inspected.

12. An apparatus as claimed in claim 8, wherein the rotary motor of the said first rotary prism (8) is in the inverse sense relative to that of said part (1) to be inspected.

13. An apparatus as claimed in claim 11, wherein the rotary motion of said second rotary prism (11) is in the inverse sense relative to that of said part (1) to be inspected.

14. An apparatus as claimed in claim 12, wherein the axis of rotation of said first rotary prism (8) forms an angle of 90 degrees with the optical axis of said first camera (5).

15. An apparatus as claimed in claim 13, wherein the axis of rotation of said second rotary prism (11) runs parallel with the optical axis of said second camera (6) or is colinear with it.

16. An apparatus for the automatic non-contact surface inspection of cylindrical parts comprising, in combination:
   a slewing mechanism (2) driven by an electric motor and accommodating and rotating said parts (1) to be inspected;
   first and second sources of light (3, 4) illuminating said parts (1) to be inspected;
   first and second electronic cameras (5, 6) respectively responding to said first and second sources of light for scanning the cylindrical surfaces of said parts (1) to be inspected one after the other at a time interval; and,
   a digital computer (7) succeeding said electronic cameras (5, 6) and serving to evaluate the image information transmitted by the latter.

17. An apparatus as claimed in claim 16, wherein said camera (5, 6) which scans the surface of the said parts (1) to be inspected is a matrix camera.

18. A process for the automatic non-contact surface inspection of cylindrical parts, comprising the steps of: imparting a rotary motion to the parts to be inspected about their axis of symmetry; exposing the barrel surfaces parts substantially parallel light whose diffused portion is reflected by the surface of said parts; scanning the surface of said parts to obtain an image of the light reflected by the surface; and evaluating the reflected image obtained from said parts optoelectronically.

19. A process as claimed in claim 18, wherein the barrel surface of the parts under inspection is exposed to the light rays at an oblique angle of preferably about 35 degrees.

20. A process as claimed in claim 18, wherein the front surface of the parts to be inspected is exposed to an axially symmetrical illumination.

21. A process as claimed in claim 20, wherein the diffused portion of light is scanned by means of an electronic camera, the parts under inspection being rotated 360 degrees during scanning.

* * * * *

UNITED STATES PATENT AND TRADEMARK OFFICE
CERTIFICATE OF CORRECTION

PATENT NO. : 5,012,117

DATED : April 30, 1991

INVENTOR(S) : Nobuyoshi KOBAYASHI et al.

It is certified that error appears in the above-identified patent and that said Letters Patent is hereby corrected as shown below:

On the title page, item [73], delete the incorrect assignee and substitute therefor --Kolb GmbH & Co., Wuppertal, Germany--.

Signed and Sealed this

Second Day of February, 1993

Attest:

STEPHEN G. KUNIN

Attesting Officer

Acting Commissioner of Patents and Trademarks